United States Patent [19]
Gutcho et al.

[11] 3,937,698
[45] Feb. 10, 1976

[54] TRITIATED DERIVATIVES OF CYCLIC NUCLEOTIDES MONOPHOSPHATES

[75] Inventors: Sidney Gutcho, Monsey; Raul Rapun, Sloatsburg, both of N.Y.; Herman Rutner, Hackensack, N.J.; Andrew Charig, Valley Cottage, N.Y.

[73] Assignee: Becton, Dickinson & Company, Rutherford, N.J.

[22] Filed: July 27, 1973

[21] Appl. No.: 383,461

[52] U.S. Cl.......... 260/211.5 R; 23/230 R; 424/180
[51] Int. Cl...................... C07d 51/52; C07d 51/54
[58] Field of Search ............................ 260/211.5 R

[56] References Cited
UNITED STATES PATENTS

| | | |
|---|---|---|
| 3,558,595 | 1/1971 | Jones et al. ................. 260/211.5 R |
| 3,712,885 | 1/1973 | Weimann et al. ............ 260/211.5 R |
| 3,751,408 | 8/1973 | Bergmeyer et al. .......... 260/211.5 R |
| 3,804,827 | 4/1974 | Robins et al. ................ 260/211.5 R |

OTHER PUBLICATIONS

Falbriard et al., "Biochim. Biophys. Acta", Vol. 148, 1967, pp. 99–105.

*Primary Examiner*—Johnnie R. Brown
*Attorney, Agent, or Firm*—Marn & Jangarathis

[57] ABSTRACT

Tritiated succinylated derivatives of cyclic nucleotides, in particular multitritiated succinylated cyclic adenosine monophosphate, useful in the radioimmunoassay of cyclic nucleotides, and maleyl derivatives of cyclic nucleotides useful in the production of the tritiated derivatives.

27 Claims, No Drawings

TRITIATED DERIVATIVES OF CYCLIC NUCLEOTIDES MONOPHOSPHATES

This invention relates to derivatives of cyclic nucleotides. More particularly, this invention relates to tritiated derivatives of cyclic nucleotides and compounds which can be employed to produce such tritiated derivatives. Still more particularly, this invention relates to tritiated derivatives of cyclic adenosine monophosphate and intermediates used in the preparation thereof.

Radioimmunoassay systems for cyclic adenosine monophosphate ($c$AMP) currently rely on either a radioiodinated derivative of $c$AMP or tritiated $c$AMP. The use of the radioiodinated derivative has the disadvantage of requiring gamma-counting capability which may not be available in many laboratories. The use of tritiated $c$AMP has the disadvantage of both inferior binding characteristics and low sensitivity inherent in the use of partially- or mono-tritiated $c$AMP. Accordingly, there is a need for new compounds which are useful in the radioimmunoassay of $c$AMP.

Accordingly, an object of the present invention is to provide tritiated derivatives of cyclic nucleotides and intermediates useful in the preparation thereof.

A further object of the present invention is to provide compounds useful for the radioimmunoassay of $c$AMP.

Another object of the present invention is to provide compounds which are useful in the preparation of compounds for the radioimmunoassay of $c$AMP.

Yet a further object of the present invention is to provide a process for producing compounds and intermediates therefor useful for the radioimmunoassay of $c$AMP.

These and other objects of the present invention should be more readily apparent from reading the following detailed description thereof.

The objects of the present invention are broadly accomplished in one aspect by providing compounds represented by the following structural formula:

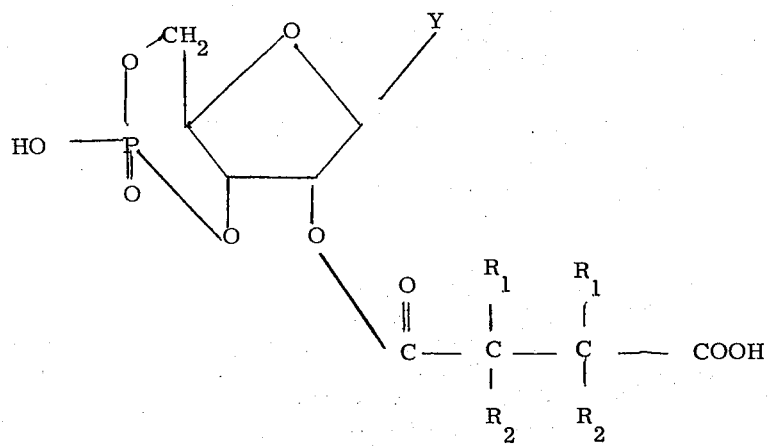

wherein each $R_1$ is either tritium, hydrogen, or lower alkyl (1–6 carbon atoms, perferably methyl) each $R_2$ is either tritium or hydrogen and at least one of $R_2$ is tritium; and Y is adenyl, guanyl, uridyl, inosyl, cytosyl, thymyl or derivatives thereof.

In the above structural formula $R_1$ and $R_2$ are preferably hydrogen or tritium with at least one of $R_2$ being tritium. Accordingly, the present invention is directed to the production of tritiated carboxyacyl derivatives, particularly multitritiated derivatives, of: cyclic adenosine 3',5'-monophosphate (cAMP); cyclic guanosine 3', 5'-monophosphate (cGMP); cyclic inosine 3',5'-monophosphate (cIMP); cyclic uridine 3',5'-monophosphate (cUMP); cyclic thymidine 3',5'-monophosphate (cTMP), and cyclic cytidine 3', 5'-monophosphate (cCMP).

The preferred compounds are the tritiated derivatives of cyclic adenosine monophosphate, as represented by the following structural formula:

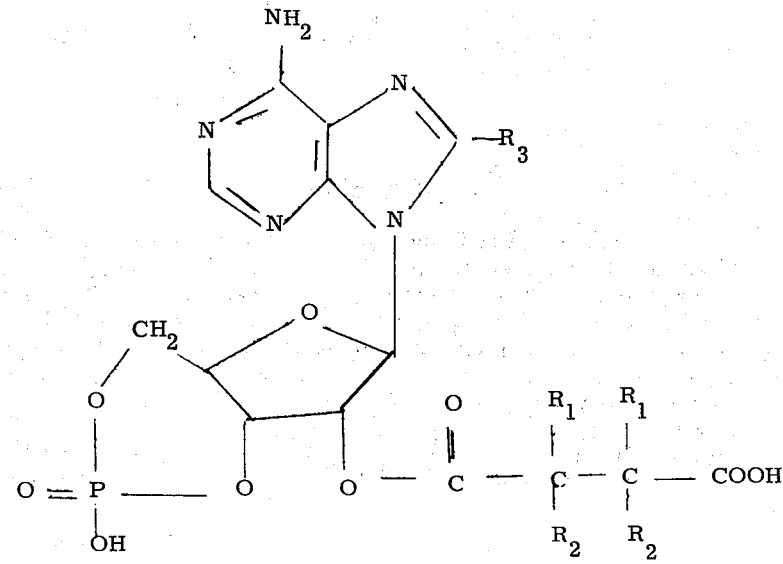

wherein $R_1$ and $R_2$ are as defined above; and $R_3$ is hydrogen or tritium as hereinabove described. The compound preferably includes two or more atoms of tritium, with $R_1$ and $R_2$ preferably being tritium or hydrogen.

The objects of the present invention are accomplished in another aspect by providing intermediates useful in the preparation of the hereinabove described tritiated derivatives, as represented by the following structural formula:

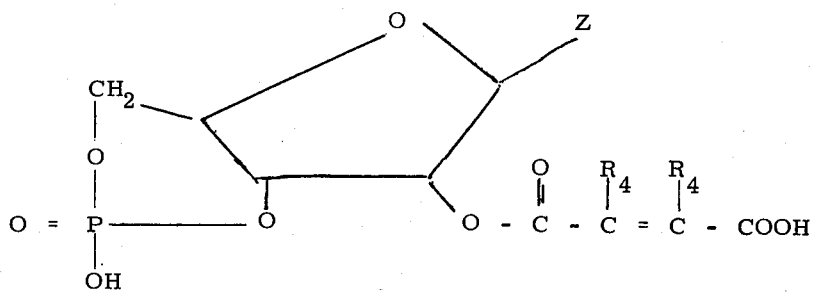

wherein $R_4$ are each either hydrogen, chloro, bromo, iodo or lower alkyl (1-6 carbon atoms preferably methyl); and Z is adenyl, guanyl, thymyl, uridyl, inosyl, cytosyl or bromo-, chloro, or iodo- substituted derivatives thereof. The preferred intermediates are derivatives of cyclic adenosine monophosphate, as represented by the following structural formula:

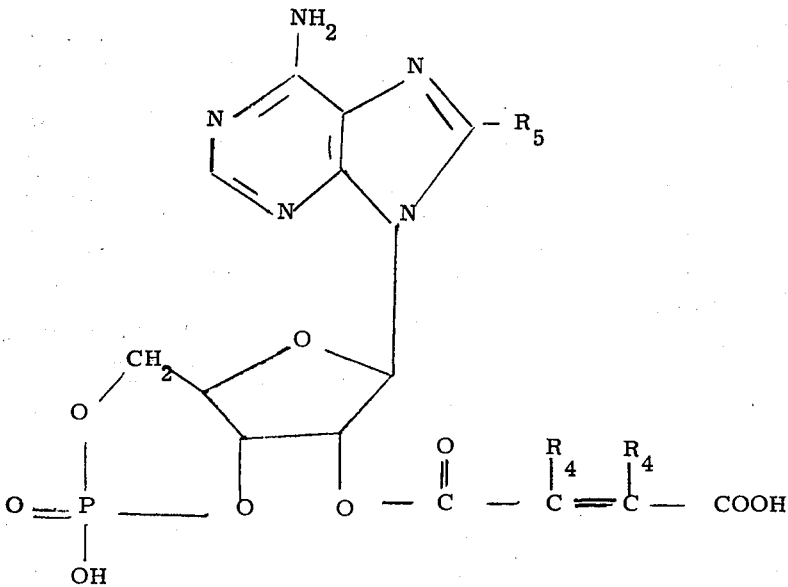

wherein $R_4$ is defined as above, and $R_5$ is hydrogen, iodo, chloro or bromo.

The present invention will be further described with respect to the production of derivatives of cyclic adenosine monophosphates which are the preferred compounds of the present invention. It is to be understood, however, that the following procedures are also applicable to the hereinabove described derivatives of other cyclic monophosphate nucleotides.

The substituted or unsubstituted maleyl derivative of cAMP intermediate in the preparation of the tritiated derivatives of the present invention, is prepared by reacting the appropriate substituted or unsubstituted maleic acid anhydride with cAMP.

In accordance with one procedure, the carboxyacyl derivative of cAMP of the present invention, is prepared by either the method disclosed by Steiner et al. *Proc. Nat. Acad. Sci.* 64 367 (1969) or the method disclosed by Falbriard et al. *Biochem. Biophys. Acta* 148 99 (1967) using the appropriate substituted or unsubstituted maleic acid anhydride instead of the succinic acid anhydride. The method basically involves the dissolution of cAMP and morpholine dicyclohexylcarbodiimide in a suitable inert solvent, such as pyridine, followed by addition of the appropriate substituted or unsubstituted maleic acid anhydride.

The substituted or unsubstituted maleyl derivative is preferably prepared in accordance with the novel procedure of the present invention. In accordance with the procedure of the present invention, cAMP is dissolved in a polar, nonprotic inert (does not react with the reactants) solvent. As representative examples of such solvents there may be mentioned, hexamethylphosphoramide, dimethylformamide, dimethylsulfoxide, acetonitrile, pyridine, dimethylacetamide and the like. THe solubilization may be facilitated by the use of non-reactive bases such as trioctylamine, tri-n-butylamine, diisopropylethylamine (Hunigs base), tetramethyl-guanidine and the like. The dissolution may be effected at a temperature from about 20°C. to about 100°C., and preferably from about 60°C. to about 80°C. The dissolution may require from one to three hours.

The substituted or unsubstituted maleyl derivative of cAMP is recovered from the reaction mixture by precipitation in the presence or absence of a solvent, such as ether, ethyl acetate, benzene, acetone, etc. followed by washing and drying in a vacuum. About 100% of the weight of cAMP started is recovered as a pale grey amorphous solid, no clear melting point. The product has the ultraviolet spectrum of cAMP, but moves slower than cAMP on DEAE cellulose TLC, and faster on cellulose TLC in a n-butanol, acetic acid and water solvent system.

The substituted or unsubstituted maleyl derivative is then tritiated by a procedure known in the art, as described for example by Rylander, 1967: *Catalytic Hydrogenation over Platinum Metals;* (Academic Press, N.Y., 1967) to produce the tritiated derivatives of cAMP of the present invention. In general, this procedure involves dissolution of the intermediate in a water-ethanol mixture buffered at a pH from 4 to 10 followed by treatment with tritium gas in the presence of a platinum group metal catalyst. This general procedure is well known in the art and can be effectively employed for tritiating the derivatives of the present invention. Accordingly, no further details in this respect are required for practicing the present invention.

The tritiated carboxyacyl derivatives, and in particular the tritiated succinylated derivatives of cGMP, cTMP, cCMP, cIMP and cUMP may be prepared by the procedures hereinabove described with respect to the production of the cAMP derivatives, by substitution of the appropriate cyclic nucleotide.

The derivatives of the present invention in which tritium is substituted in the purine or pyrimidine moiety of the cyclic nucleotide may be prepared by using, as the starting material, a cyclic nucleotide halo-substituted in the purine or pyrimidine moiety. The tritiating of the unsaturated carboxyacyl derivative of the cyclic nucleotide results in replacement of the halo group with tritium to produce the tritiated carboxyacyl derivative of the cyclic nucleotide in which the purine or pyrimidine moiety is substituted with tritium.

Similarly, the derivatives of the present invention in which more than two atoms of tritium are present in the carboxyacyl moiety are prepared from the intermediates of the present invention in which the unsaturated carboxyacyl moiety is substituted with one or more halo atoms (chloro, bromo or iodo) whereby such halo atoms can be statistically replaced with tritium in the subsequent tritiation procedure.

The derivatives of the present invention in which only one atom of tritium is present in the succinyl side chain result from the presence of hydrogen during the tritiating.

The invention will be further described with respect to the following examples but it is to be understood that the scope of the invention is not to be limited thereby. Unless otherwise specified all parts and percentages are by weight and all temperatures are °C.

EXAMPLE I

Preparation of maleyl — cAMP 200 mg. of cAMP and 200 mg. of morpholine-dicyclohexyl-carbodiimide were mixed in pyridine for a sufficient time at a temperature between 30 and 100 degrees centigrade, until all materials were dissolved. The solution was cooled to a temperature between −20° and +10°C., and maleic anhydride was added in quantities which do not cause excessive chromogenic side reactions. After thin layer chromatography on ion exchange cellulose has shown about 50 percent conversion of cAMP to a new product, with spectral qualities of cAMP, ether was added to the mixture in large excess. The precipitate, which is maleyl-cAMP, was centrifuged, washed with ether and dried in vacuum. Hydrogenation of this product yielded a material with the spectral and chromatographic characteristics of ScAMP.

EXAMPLE II

Preparation of dichloromaleyl-cAMP 100 mg. of cAMP and 100 of Hunig's base were added to 10 ml. of acetonitrile and stirred for 2 days. To the solution of cAMP was added 100 mg. of dichloromaleic anhydride, dissolved in ½ ml. of the solvent. The precipitate which is dichloromaleyl-cAMP was spun off, washed with ether, and dried in vacuum. Hydrogenation of the product yields material with the properties of ScAMP.

EXAMPLE III

Preparation of $^3$H-ScAMP

The maleyl cAMP produced in Example I was dissolved in 50% ethanol, buffered to a pH between 4 and 10 with phosphate. An equal weight of 10% palladium on carbon was added, and the mixture was exposed to 15°C. of tritium gas for a sufficient time to incorporate 500 mC of tritium into a non-volatile, stable product, which had the same chromatographic behavior of ScAMP, and which was isolated by chromatography.

The tritiated carboxyacyl derivatives of cAMP of the present invention may be employed in the radioimmunoassay of cAMP by using the procedure described by Steiner et al., *Proc. N.A.S.* Vol. 64; P. 367–373 (1969) in which the tritiated carboxyacyl derivatives of the present invention, most preferably those containing two or more tritium atoms, replace the radioiodinated tracer compound disclosed by Steiner et al. Similarly, the tritiated carboxyacyl derivatives of cCMP, cUMP, cTMP, cGMP and cIMP may be used for the radioimmunoassay of the corresponding cyclic nucleotide by the procedure described by Steiner et al, *J. Bio. Chem.* Vol. 247, pp. 1106–13 (1972) in which the tritiated derivatives of the present invention replace the radioiodinated tracer compound disclosed by Steiner et al.

The tritiated derivatives of the present invention are particularly advantageous for the radioimmunoassay of cyclic nucleotides as a result of having superior immuno-reactivity and higher specific activity. In addition, the multitritiated derivatives are superior to the radioiodinated derivatives, as disclosed by Steiner et al, in that the radioatom is substituted on a side chain which is less bulky and which involves less modification of the cyclic nucleotide.

Numerous modifications and variations of the present invention are possible in light of the above teachings and, therefore, within the scope of the appended claims the invention may be practiced in a manner otherwise than as particularly described.

What is claimed:

1. A compound selected from the group consisting of compounds represented by the following structural formula I:

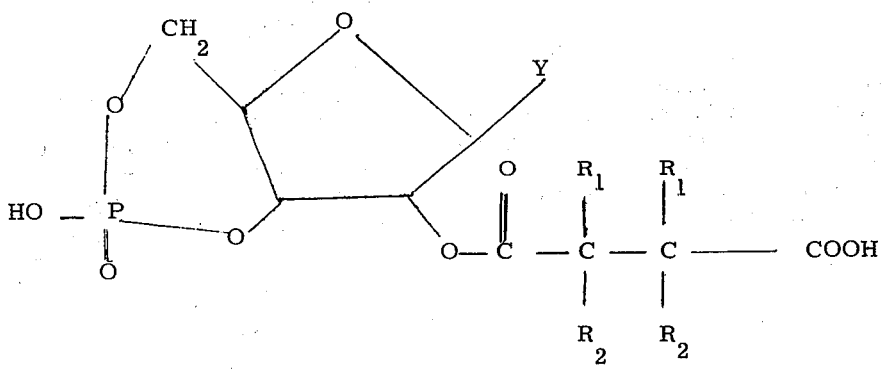

I wherein
Y is selected from the group consisting of inosyl, adenyl, uradyl, guanyl, thymyl, cytidyl and the tritium substituted derivatives thereof;
each $R_1$ is selected from the group consisting of hydrogen, tritium and lower alkyl; and
each $R_2$ is selected from the group consisting of tritium and hydrogen with at least one $R_2$ being tritium;

and compounds having the following structural formula II:

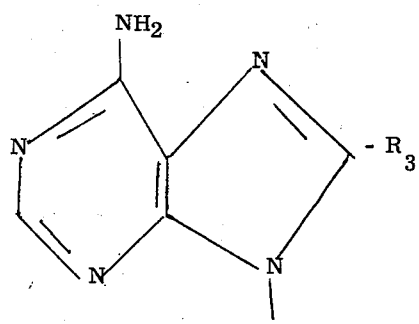

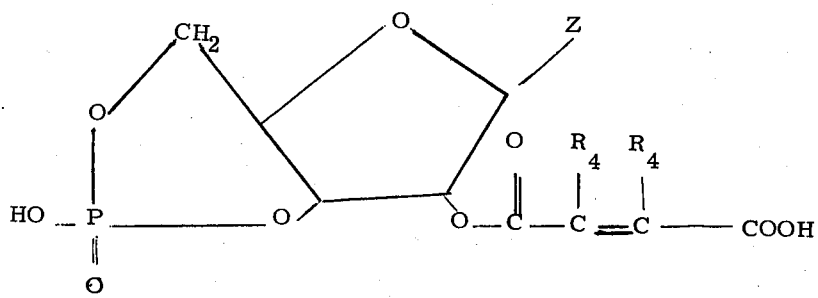

II wherein
Z is selected from the group consisting of uradyl, guanyl, inosyl, thymyl, adenyl, cytidyl and the chloro-, bromo and iodo- substituted derivatives thereof; and
each $R_4$ is selected from the group consisting of hydrogen, chloro, iodo, bromo, and lower alkyl.

2. The compound of claim 1 wherein the compound is represented by structural formula I.

3. The compound of claim 2 wherein each $R_1$ and $R_2$ is selected from the group consisting of hydrogen and tritium wherein said compound contains at least two atoms of tritium.

4. The compound of claim 3 wherein Y is inosyl.
5. The compound of claim 3 wherein Y is uradyl.
6. The compound of claim 3 wherein Y is guanyl.
7. The compound of claim 3 wherein Y is thymyl.
8. The compound of claim 3 wherein Y is cytidyl.
9. The compound of claim 2 wherein Y is wherein
$R_3$ is selected from the group consisting of hydrogen and tritium.

10. The compound of claim 9 wherein $R_3$ is hydrogen.

11. The compound of claim 10 wherein $R_1$ and $R_2$ are each selected from the group consisting of hydrogen and tritium and wherein the compound contains at least two atoms of tritium.

12. The compound of claim 9 wherein $R_3$ is tritium.

13. The compound of claim 12 wherein $R_1$ and $R_2$ are each selected from the group consisting of hydrogen and tritium and wherein at least one of $R_2$ is tritium.

14. The compound of claim 1 wherein the compound is represented by Structural formula II.

15. The compound of claim 14 wherein each $R_4$ is hydrogen.

16. The compound of claim 14 wherein each $R_4$ is chloro.

17. The compound of claim 14 wherein Z is uradyl.
18. The compound of claim 14 wherein Z is thymyl.
19. The compound of claim 14 wherein Z is inosyl.
20. The compound of claim 14 wherein Z is cytidyl.
21. The compound of claim 14 wherein Z is guanyl.
22. The compound of claim 14 wherein Z is

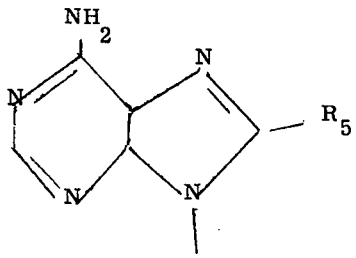

wherein
$R_5$ is selected from the group consisting of hydrogen, bromo, chloro, and iodo.
23. The compound of claim 22 wherein $R_5$ is hydrogen.
24. The compound of claim 23 wherein each $R_4$ is hydrogen.
25. The compound of claim 23 wherein each $R_4$ is chloro.
26. The compound of claim 22 wherein each $R_4$ is chloro.
27. The compound of claim 22 wherein each $R_4$ is hydrogen.

* * * * *